(12) United States Patent
Frot

(10) Patent No.: US 6,975,388 B2
(45) Date of Patent: Dec. 13, 2005

(54) OPTICAL-FIBER REFRACTOMETER

(75) Inventor: Didier Frot, Choisy le Roi (FR)

(73) Assignee: Institut Francais du Petrole (FR)

( * ) Notice: Subject to any disclaimer, the term of this patent is extended or adjusted under 35 U.S.C. 154(b) by 321 days.

(21) Appl. No.: 10/290,513

(22) Filed: Nov. 8, 2002

(65) Prior Publication Data
US 2003/0095248 A1 May 22, 2003

(30) Foreign Application Priority Data
Nov. 16, 2001 (FR) .............................. 01 14815

(51) Int. Cl.$^7$ ................................................ G01N 21/41
(52) U.S. Cl. ....................................... 356/128; 356/133
(58) Field of Search ............................... 356/128–137, 356/445–448

(56) References Cited

U.S. PATENT DOCUMENTS

| 3,999,857 | A | * | 12/1976 | David et al. ................. 356/133 |
| 4,361,402 | A | * | 11/1982 | Costa ......................... 356/73.1 |
| 4,699,511 | A | | 10/1987 | Seaver |
| 5,357,333 | A | * | 10/1994 | DeBernardi et al. ....... 356/73.1 |
| 5,831,743 | A | | 11/1998 | Ramos et al. |
| 5,956,132 | A | * | 9/1999 | Donzier ...................... 356/133 |
| 6,304,328 | B1 | * | 10/2001 | Longtin ...................... 356/445 |
| 6,559,951 | B2 | * | 5/2003 | Ishikawa et al. ........... 356/517 |

FOREIGN PATENT DOCUMENTS

| EP | 0 809 098 A1 | 11/1997 |
| FR | 2 725 788 | 1/1997 |
| WO | WO 82/03460 | * 10/1982 |
| WO | WO 90/01697 | 2/1990 |

* cited by examiner

Primary Examiner—Michael P. Stafira
(74) Attorney, Agent, or Firm—Antonelli, Terry, Stout and Kraus, LLP

(57) ABSTRACT

The invention relates to a refractometer and to a method of measuring the refractive index of a medium. An incident light ray is directed onto an interface consisting of a medium of known refractive index and of the medium being studied. Then the intensity of the reflected light ray is measured. The incident and reflected light rays are propagated in an optical fiber section. The ratio between the intensity of the incident ray and the intensity of the reflected ray allows the refractive index of the medium studied to be calculated by means of Fresnel's formulas.

10 Claims, 1 Drawing Sheet

OPTICAL-FIBER REFRACTOMETER

BACKGROUND OF THE INVENTION

1. Field of the Invention

The invention relates to the determination of a refractive index, in particular the refractive index of an oil at the bottom of a well. It provides a method and a refractometer intended for absolute measurement of the refractive index.

2. Description of the Prior Art

French Patent application 2,825,151 provides a method for measuring the refractive index of a medium.

SUMMARY OF THE INVENTION

This invention is based on a measuring principle using the phenomenon of reflection of a light ray on an interface. The present invention provides another refractometer and another methodology using the same measuring principle.

In general terms, the invention provides a refractometer comprising:

a light source emitting an incident light ray in the direction of an interface consisting of a first medium of unknown refractive index and of a second medium of known refractive index;

a first detector measuring the intensity of a light ray reflected on the interface; and a first optical fiber section in which the incident light ray and the reflected light ray are propagated.

The end of the first optical fiber section of the refractometer according to the invention can be provided with a glass element.

A T-coupler can transfer the incident light ray from the light source to the first optical fiber section and transfer the reflected light ray from the first optical fiber section to the first detector. A second optical fiber section can be arranged between the light source and the T-coupler with the incident ray propagating in the second optical fiber section. A third optical fiber section can be arranged between the T-coupler and the first detector with the reflected light ray propagating in the third optical fiber section.

A lens can concentrate the incident light ray prior to entering the second optical fiber section.

A plate can be arranged between the light source and the first optical fiber section, the plate allowing a light ray to be divided into two light rays. A light ray emitted by the source can be divided by the plate so as to form the incident light ray and a reference light ray with the intensity of the reference light ray being measured by a detector.

The refractometer according to the invention can be used to determine the refractive index of a petroleum effluent at the bottom of a petroleum production well by arranging the various constituent elements of the refractometer as follows:

the first medium is the petroleum effluent at the well bottom;

the light source and the first detector are located at the surface of the well; and the first optical fiber section extends from the well bottom to the well surface.

The invention also provides a method of measuring the refractive index of a first medium. The method comprises the following steps:

directing an incident light ray onto an interface consisting of the first medium and a second medium of known refractive index so as to produce a reflected light ray arranging a first optical fiber section in which the incident light ray and the reflected light ray are propagated measuring the intensity of said incident light ray and the intensity of said reflected light ray; and determining the refractive index of the first medium by taking account of at least the refractive index of the second medium, the intensity of the incident light ray and the intensity of the reflected light ray.

Implementation of the method according to the invention allows determination of the refractive index of the first medium by means of a formula relating the intensity of the incident light ray to the intensity of the reflected light ray at the level of the interface by accounting for the refractive index of the first medium and of refractive index of the second medium. The refractive index of the first medium is for example determined with Fresnel's formulas.

A source light ray can be divided so as to form a reference light ray and incident light ray.

According to the invention, a first medium whose refractive index is known can be used. In this configuration, the intensity of the reference light ray and the intensity of the reflected light ray are measured in order to determine the ratio of the intensity of the reference light ray divided by the intensity of the incident light ray using a formula that relates the intensity of the incident light ray to the intensity of the reflected light ray at the level of the interface by accounting for the refractive indices of the first and of the second mediums.

The intensity of the reference light ray can be measured to determine the intensity of the incident light ray.

With an optical fiber allowing a light ray to be guided without its characteristics being altered, it is possible to move the light source and the detectors away from the medium studied on demand. For example, it is possible to measure the refractive index of an effluent located at the well bottom by arranging the light source and the detectors at the surface. Thus, the refractometer and the method according to the present invention notably afford the advantage of enabling measurement of the refractive index of a fluid under high pressure and high temperature. The only element of the refractometer in contact with the fluid studied is an optical fiber section, and the end of the section can be made of glass. The operating limits of the refractometer as regards the temperature and the pressure of the fluid studied are therefore equal to the temperature and pressure resistance limits of the optical fiber section, possibly provided with a glass end in contact with the fluid studied.

BRIEF DESCRIPTION OF THE DRAWINGS

Other features and advantages of the invention will be clear from reading the description hereafter of embodiments given by way of non limitative example, with reference to the accompanying drawings wherein.

DETAILED DESCRIPTION OF THE INVENTION

Figure 1:
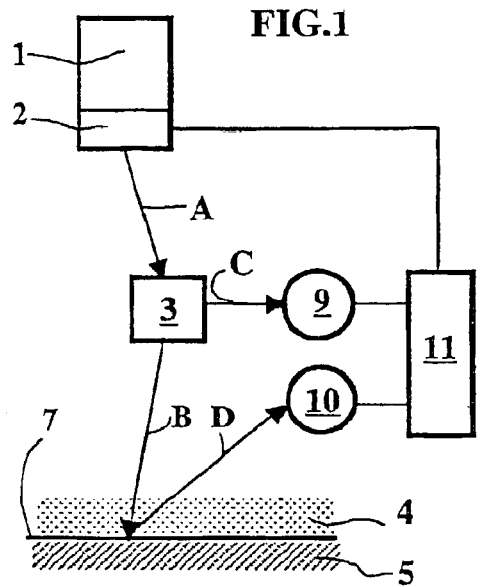
FIG. 1 shows the working principle of a refractometer according to the invention, FIG. 2 diagrammatically shows the phenomenon of refraction and reflection of a light ray directed onto an interface, FIG. 3 diagrammatically shows a refractometer according to the invention.

In FIG. 1, the refractometer comprises a light source 1. Light source 1 emits a monochromatic light ray A, by means of a filter for example. The stability of the light ray emitted is $10^{-1}$ in relation to the intensity emitted. The light source can be a laser diode, or laser, emitting a light ray whose intensity is approximately 5 mW. The light source is associated with coding means 2. Coding means 2 allows light ray A to be coded. For example, coding means 2 allows the intensity of the light ray A to periodically vary, at a frequency f1, in a sinusoidal manner for example, around a mean value. Furthermore, coding means 2 allows the mean intensity of light ray 2 to periodically vary, at a frequency f2, for example with a square wave. Frequency f1 can be 5000 Hz and frequency f2 can be 1 Hz.

Light ray A is divided by an optical element 3 into two light rays: light ray B and light ray C. The sum of the intensities of light rays B and C is equal to the intensity of light ray A. Furthermore, the intensities of light rays B and C vary according to frequencies identical to those of light ray A.

Light ray B is propagated to interface 7. Interface 7 is the interface between medium 4, whose refractive index is known, and medium 5 whose refractive index is to be measured. In FIG. 1, medium 4 is represented by the area covered with dots and medium 5 is represented by the hatched area. Interface 7 can be plane. Light ray D represents the part of light ray B reflected on interface 7.

Photodetectors 9 and 10 are respectively arranged on the paths of light rays C and D. Photodetector 9 measures the intensity of light ray C and photodetector 10 measures the intensity of light ray D.

A signal processor 11 is connected to coding means 2 and to photodetectors 9 and 10. The second processor allows decoding the signals picked up by photodetectors 9 and 10, considering the coding performed by coding means 2, then to compare and to analyse the intensities measured by photodetectors 9 and 10. Photodetectors 9 and 10 measure, on the one hand, the intensities of light rays B and C from light ray A and, on the other hand, parasitic intensities that have no connection with light ray A. By means of the coding means 2, light rays B and C vary periodically according to frequencies f1 and f2. These data are transmitted to the signal processor 11. Thus, by seeking light intensities that vary periodically according to frequencies f1 and f2, the signal processor 11 can detect and isolate the intensities of light rays C and D among the light intensities measured by photodetectors 9 and 10. Then, the signal processor 11 can compare the intensities of light rays C and D.

Figure 2:
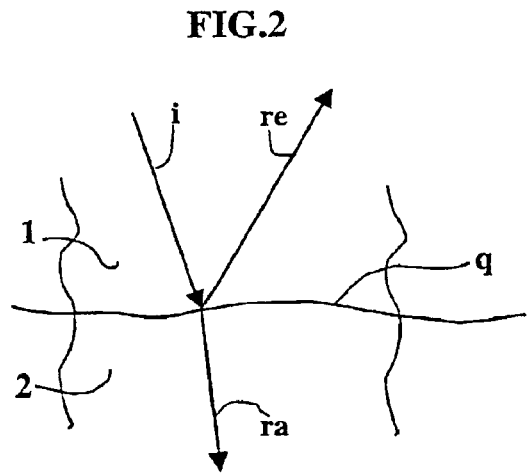

The measuring principle according to the present invention uses the phenomenon of reflection of a light ray to determine the refractive index of a medium. In connection with FIG. 2, Fresnel's formulas connect the intensity Ii of incident ray i to the intensity Ire of reflected ray re at the level of an interface q as a function of the refractive indices n1 and n2 of the two media 1 and 2 which form interface q. When the angle of incident ray i on interface q is 90°, Fresnel's formulas are written in form of a single expression:

$$\frac{I_i}{I_r} = \frac{\left[\left(\frac{n_2}{n_1}\right) - 1\right]^2}{\left[\left(\frac{n_2}{n_1}\right) + 1\right]^2}$$

Without departing from the scope of the invention, it is possible to use any formula equivalent to Fresnel's formulas which describes the phenomenon of reflection on an interface regarding the intensities of the incident and reflected rays, by accounting for the refractive indices of the two media which make up the interface.

According to the invention, by measuring the intensity IC of ray C and knowing the distribution of the intensity IA of ray A between rays B and C by optical element 3, the intensity IB of ray B is determined. The distribution of the intensity IA of ray A between rays B and C can be expressed by the value of the ratio of the intensity IC of ray C divided by the intensity IB of ray B, that is ratio $$\frac{IC}{IB}.$$

By measuring the intensity IC of ray C to know the intensity IB of ray B, a more accurate measurement is obtained because the value of intensity IC is comparable to intensity ID.

After determining the intensity IB of light ray B, by measuring the intensity ID of light ray D and knowing the refractive index n4 of medium 4, the refractive index n5 of the studied medium 5 is determined by means of Fresnel's formulas.

In order to precisely determine, on passage of ray A into optical element 3, the value of the ratio of the intensity IC of light ray C divided by the intensity IB of light ray B, that is ratio $$\frac{IC}{IB},$$

a medium 5 of known refractive index n5 is placed in the refractometer according to the invention. Using Fresnel's formulas, knowing the refractive indices n4 and n5 of media 4 and 5, and by measuring the intensity ID of light ray D, the intensity IB of light ray B is determined. Since the intensity IC of light ray C is measured, the ratio of intensity IC divided by intensity IB is known with precision, this ratio $$\frac{IC}{IB}$$

being used for implementing the refractometer according to the invention in order to determine the refractive index of a medium 5. This ratio is known as the "calibration number" of the measuring device.

Figure 3:
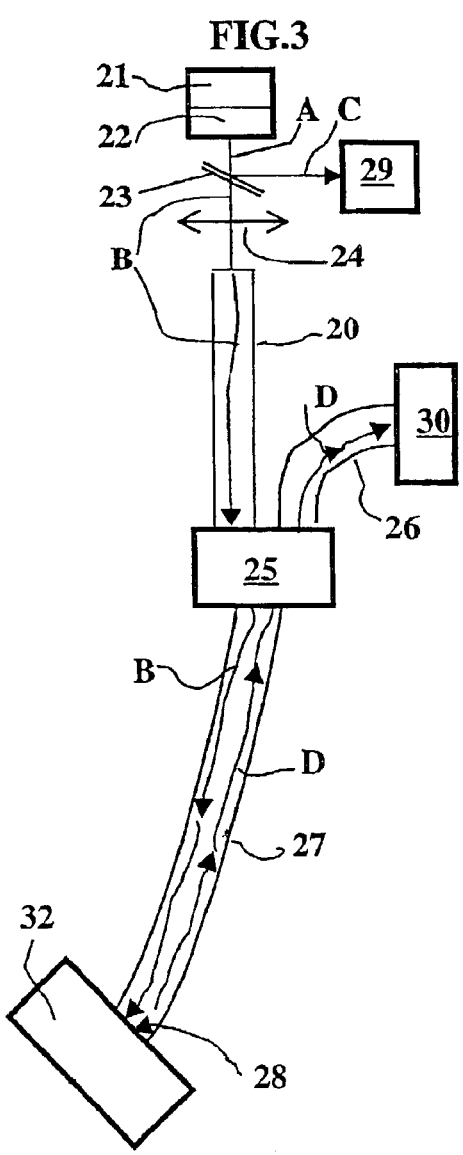

FIG. 3 shows an embodiment of the refractometer according to the invention wherein the light rays are guided by optical fibers.

Light source 21 emits a main light ray A. A coding means 22 codes main light ray A.

Ray A is directed onto a plate 23. At the level of the plate, ray A is divided into two light rays: light ray C and light ray B. Light ray B is the part of main light ray A that passes through plate 23. Light ray C is the part of main light ray A that is reflected by plate 23. The intensity of light ray C is measured by photodetector 29. Light ray B is concentrated by means of lens 24 prior to being introduced into a first optical fiber section 20. Ray B propagates in optical fiber section 20 up to T-coupler 25. T-coupler 25 is connected to three optical fiber sections: optical fiber 20, optical fiber 26 and optical fiber 27. T-coupler 25 allows a transfer of light ray B from fiber 20 to fiber 27 and a transfer of light ray D from fiber 27 to fiber 26. Rays B and D are respectively propagated in fibers 20 and 27 in the direction of T-coupler 25.

Light ray B propagates in optical fiber section 27 from T-coupler 25 to the end 28 of section 27. End 28 can be provided with a glass element 32 ensuring pressure, temperature and corrosion resistance of optical fiber section 27. End 28 provided with element 32 is dipped into the medium to be studied. At end 28, light ray B is reflected by the interface of the end 28 of optical fiber section 27 and of the medium studied. If end 28 is provided with glass element 32, light ray B is reflected by the interface of glass element 32 and of the medium studied. The reflected ray D propagates in optical fiber section 27 from end 28 up to T-coupler 25. Ray D is transferred from optical fiber section 27 to optical fiber section 26 by means of T-coupler 25. In section 26, ray D propagates from T-coupler 25 up to photodetector 30. Photodetector 30 allows measurement of the light intensity of ray D when it comes out of optical fiber section 26.

Figure 4:
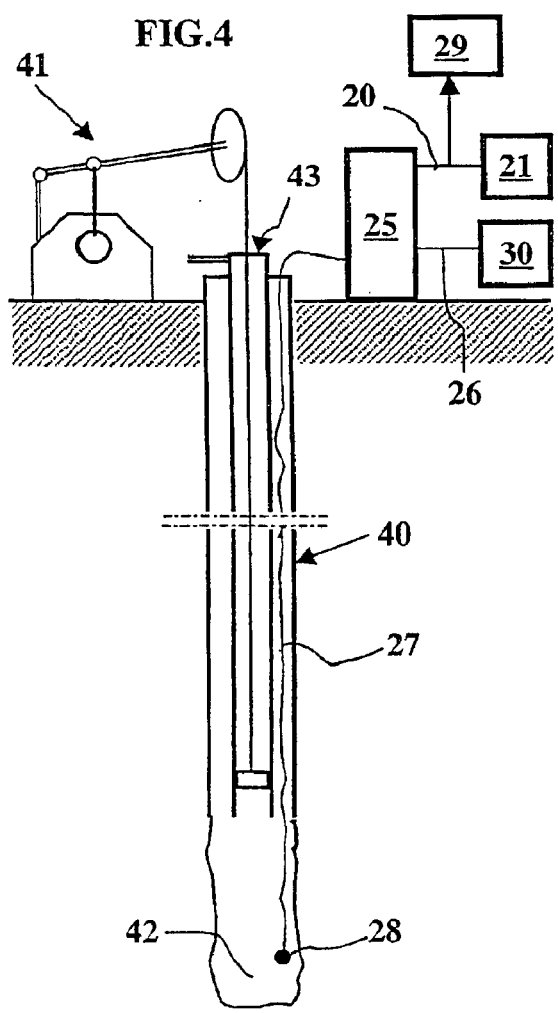
FIG. 4 shows an implementation of a refractometer according to the invention.

The refractometer according to the invention allows measurement of the refractive index of a fluid that is not very accessible. For example, the refractometer can measure the refractive index of a petroleum effluent at the bottom of a well. FIG. 4 shows an oil well 40. Pumping device 41 allows pumping of the oil from well bottom 42 to wellhead 43 at the surface. A refractometer according to the invention (the reference numbers of FIG. 4 similar to those of FIG. 3 designate identical elements) allows measurement of the refractive index of the oil located at the bottom 42 of well 40. Light source 21, optical fiber sections 20 and 26, T-coupler 25 and photodetectors 29 and 30 are arranged at the surface, preferably close to wellhead 43. End 28 of optical fiber section 27, located at the bottom 42 of the well, is dipped in the effluent (end 28 can be protected by a glass element 32). Optical fiber 27 thus allows establishing a connection between end 28 at the bottom 42 of well 40 and T-coupler 25 at the surface.

What is claimed is:

1. A refractometer comprising:

a light source emitting a source light ray;

a plate dividing the source light ray in order to form an incident light ray and a reference light ray;

a first optical fiber section in which the incident light ray and a reflected light ray are propagated, the reflected light ray resulting from reflection of the incident light ray on an interface of a first medium of unknown refractive index and of a second medium of known refractive index, the interface being disposed at one end of the first optical fiber section;

a first detector for measuring intensity of the reflected light ray; and a second detector for measuring intensity of the reference light ray; and wherein the first medium is the petroleum effluent at a bottom of a well;

the light source and the first detector are disposed at a surface of the well; and the first optical fiber section extends from the bottom up to the surface.

2. A refractometer as claimed in claim 1, wherein an end of the first optical fiber section is provided with a glass element.

3. A refractometer as claimed in claim 1, comprising a T-coupler allowing transfer of incident light ray from the plate to the first optical fiber section and to transfer the reflected light ray from the first optical fiber section to the first detector.

4. A refractometer as claimed in claim 3, comprising a second optical fiber section disposed between light source and T-coupler and wherein the incident ray is propagated in the second optical fiber section.

5. A refractometer as claimed in claim 3, comprising a third optical fiber section disposed between T-coupler and first detector and wherein the reflected light ray is propagated in the third optical fiber section.

6. A refractometer as claimed in claim 4, comprising a lens which concentrates the incident light ray prior to entering the second optical fiber section.

7. A method of measuring a refractive index of a first medium, comprising;

directing a source light ray onto a plate dividing a source light ray in order to form an incident light ray and a reference light ray;

providing a first optical fiber section in which the incident light ray and a reflected light ray are propagated and where the reflected light ray resulting from reflection of the incident light ray on an interface of the first medium and of a second medium of known refractive index;

measuring intensity of the reference light ray and intensity of the reflected light ray; and determining a refractive index of the first medium by accounting for at least the refractive index of the second medium, intensity of the incident light ray and the intensity of the reflected light ray; and wherein the first medium whose refractive index is known is used, an intensity of the reference light ray and of the reflected light ray are measured and a ratio of the intensity of the reference light ray divided by the intensity of the incident light ray is determined using a formula relating intensity of the incident light ray to the intensity of the light ray reflected at a level of the interface by accounting for refractive indices of the first medium and of the second medium.

8. A method as claimed in claim 7, wherein the refractive index of the first medium is determined by a formula relating intensity of the incident light ray to the intensity of the reflected light ray at the level of the interface, by accounting for the refractive index of the first medium and of the refractive index of the second medium.

9. A method as claimed in claim 8, wherein the refractive index of the first medium is determined with Fresnel's formulas.

10. A measuring method as claimed in claim 7, wherein the intensity of the reference light ray is measured to determine the intensity of the incident light ray.

* * * * *